United States Patent [19]

Bollag et al.

[11] 4,044,051

[45] Aug. 23, 1977

[54] 9[2-(1-ALKOXY-ETHYL)-5,5-DIMETHYL-CYCLOPENT-1-EN-1-YL]-3,7-DIMETHYL-NONA-2,4,6,8-TETRAEN ACID COMPOUNDS

[75] Inventors: Werner Bollag, Basel; Norbert Rigassi, Arlesheim; Ulrich Schwieter, Reinach, all of Switzerland

[73] Assignee: Hoffmann-La Roche Inc., Nutley, N.J.

[21] Appl. No.: 596,499

[22] Filed: July 16, 1975

Related U.S. Application Data

[63] Continuation of Ser. No. 314,998, Dec. 14, 1972, abandoned.

Foreign Application Priority Data

[30]

Dec. 22, 1971 Switzerland ............... 18721/71

[51] Int. Cl.$^2$ ............... A61K 31/19; C07C 53/00; C07C 61/38; C07C 63/04
[52] U.S. Cl. ............... 260/514 R; 260/468 L; 260/469; 260/476 R; 260/488 A; 260/586 R; 260/514 L; 260/597 R; 424/299; 424/308; 424/311; 424/314; 424/317; 424/339; 424/341
[58] Field of Search ......... 260/514 D, 514 K, 514 L

[56] References Cited

U.S. PATENT DOCUMENTS

| 2,451,739 | 10/1948 | Isler | 260/488 A |
|---|---|---|---|
| 2,540,118 | 2/1951 | Isler | 260/488 A X |
| 2,576,103 | 11/1951 | Cawley et al. | 260/468 L X |
| 2,576,104 | 11/1951 | Shantz et al. | 260/514 L X |
| 2,591,110 | 4/1952 | Weisler | 260/468 L X |
| 2,680,755 | 6/1954 | Robeson et al. | 260/468 L X |
| 3,069,460 | 12/1962 | Eiter | 260/468 L X |
| 3,247,239 | 4/1966 | Truscheit et al. | 260/468 L |
| 3,505,386 | 4/1970 | Babcock et al. | 260/468 L |
| 3,639,463 | 2/1972 | Pike et al. | 260/488 R |
| 3,755,565 | 8/1973 | Spraggins | 260/514 D |
| 3,755,599 | 8/1973 | Rosenthale et al. | 260/514 D X |

OTHER PUBLICATIONS

Bollag et al., Chemical Abstracts, vol. 76, p. 475, No. 99874s (1972).
Shenk, Chemical Abstracts, vol. 75, p. 381 (1971).
Van aen Tempel et al., Chemical Abstracts, vol. 64, 8245c (1966).

*Primary Examiner*—Floyd D. Higel
*Attorney, Agent, or Firm*—Samuel L. Welt; Bernard S. Leon; Richard A. Gaither

[57] ABSTRACT

9-[2-(1-alkoxy-ethyl)-5,5-dimethyl-cyclopent-1-en-1-yl]-3,7-dimethyl-nona-2,4,6,8-tetraen acid compounds are disclosed which are useful for the topical or systemic treatment of dermatological disorders.

3 Claims, No Drawings

9-[2-(1-ALKOXY-ETHYL)-5,5-DIMETHYL-CYCLO-PENT-1-EN-1-YL]-3,7-DIMETHYL-NONA-2,4,6,8-TETRAEN ACID COMPOUNDS

This is a continuation, of application Ser. No. 314,998, filed Dec. 14, 1972, now abandoned entitled "CYCLOPENT-1-ENE DERIVATIVES."

SUMMARY OF INVENTION

In accordance with this invention, it has been found that compounds of the formula

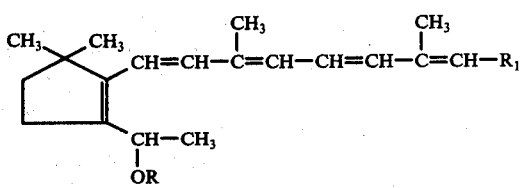

wherein R is lower alkyl, lower alkanoyl, or aroyl; and $R_1$ is hydroxymethylene, alkanoyloxymethylene, aroyloxymethylene, carboxyl, alkoxycarbonyl or aralkoxycarbonyl are useful in the treatment, by either systemic or topical modes, of certain disorders of the skin.

The compounds of formula I are prepared through the oxidation of vitamin A acid compounds of the formula

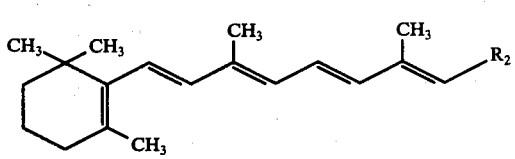

wherein $R_2$ is carboxy, alkoxycarbonyl or aralkoxycarbonyl.

DETAILED DESCRIPTION OF THE INVENTION

As used herein the term "lower alkyl" signifies both straight and branched chain hydrocarbon groups containing from 1 to 6 carbon atoms such as methyl, ethyl, isopropyl, etc. The term "lower alkanoyl" signifies both straight chain and branched chain alkanoyl groups containing from 2 to 6 carbon atoms such as acetyl, propionyl, pivaloyl, etc. The term "aroyl" designates aroyl groups derived from aromatic carboxylic acids containing from 7 to 12 carbon atoms. Generally the preferred aroyl groups are benzoyl or benzoyl substituted in one or more positions with an alkyl group having from 1 to 4 carbon atoms. Among those aroyl groups particularly preferred are benzoyl, toluoyl or xyloyl.

The term "lower alkoxy" designates both straight and branched chain alkoxy groups containing from 1 to 6 carbon atoms such as methoxy, ethoxy, isopropoxy, etc.

The alkanoyloxy moiety of the alkanoyloxymethylene groups is preferably derived from a lower alkanecarboxylic acid containing from 2 to 6 carbon atoms (e.g., acetic acid or propionic acid), but it can, however, also be derived from a higher alkanecarboxylic acid containing from 7 to 20 carbon atoms (e.g., palmitic acid or stearic acid). The aroyloxy moiety of the aroyloxymethylene groups is preferably derived from an aromatic carboxylic acid containing from 7 to 11 carbon atoms (e.g., benzoic acid, toluic acid or xylic acid). The preferred aroyloxymethylene group is the benezoyloxymethylene group. The alkoxycarbonyl groups preferably contain lower alkoxy groups containing from 1 to 6 carbon atoms. They can be straight chain or branched chain such as, for example, the methoxy, ethoxy or isopropoxy groups. However, the alkoxycarbonyl groups can contain higher alkoxy groups containing from 7 to 20 carbon atoms, especially the cetyloxy group. The aralkoxycarbonyl groups preferably contain 8 to 12 carbon atoms. Of these, the benzyloxycarbonyl group is preferred.

Examples of polyene compounds of formula I above are:

9-[2-(1-methoxyethyl)-5,5-dimethyl-cyclopent-1-en-1-yl]-3,7-dimethyl-nona-2,4,6,8-tetraen-1-acid;

9-[2-(1-ethoxyethyl)-5,5-dimethyl-cyclopent-1-en-1-yl]-3,7-dimethyl-nona-2,4,6,8-tetraen-1-acid;

9-[2-(1-methoxyethyl)-5,5-dimethyl-cyclopent-1-en-1-yl]-3,7-dimethyl-nona-2,4,6,8-tetraen-1-acid methyl ester;

9-[2-(1-ethoxyethyl)-5,5-dimethyl-cyclopent-1-en-1-yl]-3,7-dimethyl-nona-2,4,6,8-tetraen-1-acid ethyl ester;

9-[2-(1-methoxyethyl)-5,5-dimethyl-cyclopent-1-en-1-yl]-3,7-dimethyl-nona-2,4,6,8-tetraen-1-ol;

9-[2-(1-ethoxyethyl)-5,5-dimethyl-cyclopent-1-en-1-yl]-3,7-dimethyl-nona-2,4,6,8-tetraen-1-ol;

9-[2-(1-acetoxyethyl)-5,5-dimethyl-cyclopent-1-en-1-yl]-3,7-dimethyl-nona-2,4,6,8-tetraen-1-acid;

9-[2-(1-propionyloxyethyl)-5,5-dimethyl-cyclopent-1-en-1-yl]-3,7-dimethyl-nona-2,4,6,8-tetraen-1-acid; and 9-[2-(1-acetoxyethyl)-5,5-dimethyl-cyclopent-1-en-1-yl]-3,7-dimethyl-nona-2,4,6,8-tetraen-1-acetate.

In accordance with this invention, the compound of formula II is converted to the compound of formula I via an intermediate of the formula

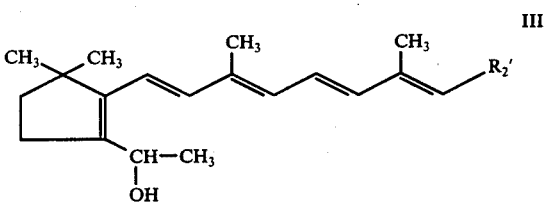

wherein $R_2'$ is hydroxymethylene, carboxyl, alkoxycarbonyl or aralkoxycarbonyl.

The compound of formula III is converted to the compound of formula I by etherification or esterification with a compound furnishing the group R and, if desired, esterifying or reducing the acid obtained or, if desired, hydrolyzing or reducing an ester obtained and, also if desired, esterifying an alcohol obtained from an acid or ester.

In the first step of producing a compound of formula III, the compound of formula II is oxidized with the aid of a strong oxidation agent, especially with the aid of chromosulfuric acid (chromium trioxide/aqueous sulfuric acid) in the presence of an inert organic solvent. In carrying out this reaction, any conventional inert organic solvent such as acetone or tetrahydrofuran can be utilized. In carrying out this reaction, temperatures of from −15° to 30° C. can be utilized. This oxidation reaction produces a compound of the formula

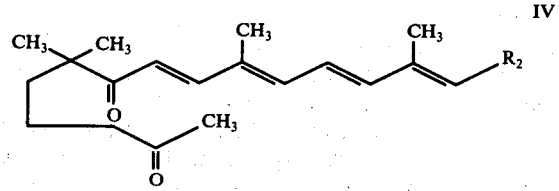

wherein $R_2$ is as above.

The compound of formula IV remains in solution after separation of crystalline by-products. The compound of formula IV can be purified by crystallization or by adsorption on silica gel or aluminum oxide (elution agent: hexane/ethyl acetate — 3:1 parts of volume).

The diketones of formula IV obtained are next cyclized to the corresponding anhydro compounds of the general formula

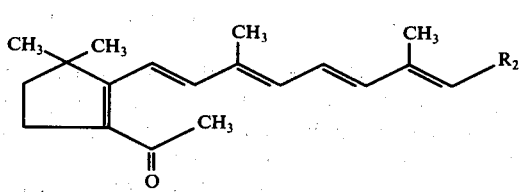

wherein $R_2$ is as above
either by treatment with a base (e.g., aqueous alcoholic sodium hydroxide or potassium hydroxide) or with an acid (e.g., a mineral acid such as perchloric acid or sulfuric acid or a strong organic acid such as p-toluenesulfonic acid, formic acid, acetic acid or oxalic acid), if necessary in an organic solvent (e.g., benzene, tetrahydrofuran or methylene chloride, but especially in benzene with water-cleavage). Both the basic cyclization and the acidic cyclization is carried out at a temperature from about room temperature to the refluxing temperature of the cyclization mixture.

Diketones of formula IV in which $R_2$ is an alkoxycarbonyl group are saponified to the corresponding acid under the conditions of the basic cyclization. The 9-[2-acetyl-5,5-dimethyl-cyclopent-1-en-1-yl]-3,7-dimethyl-nona-2,4,6,8-tetraen-1-acid (anhydroretinone acid) of formula V is crystalline as are the corresponding esters which are obtained by an acidic cyclization. The anhydro compounds of formula V can be purified by recrystallization (e.g., from an alcohol such as methanol) or by adsorption on silica gel or aluminum oxide (elution agent: hexane/ethyl acetate — 1:1 parts by volumes in the case of the acid and 3:1 parts by volume in the case of esters).

An anhydro compound of formula V is subsequently reduced to a desired starting material of formula III in which $R_2'$ is carboxyl, aralkoxycarbonyl or alkanoyloxycarbonyl in a manner known per se; for example, using an alkali metal hydride reducing agent especially a borohydride. The reduction is conveniently carried out using an alkali metal borohydride, especially sodium borohydride, in a lower alkanol such as methanol at a temperature between room temperature and the reflux temperature of the reduction mixture.

If the foregoing reduction is carried out using lithium aluminum hydride, then not only is the acetyl group reduced to the 1-hydroxyethyl group but at the same time an alkoxycarbonyl group which may be present as $R_2$ is reduced to the hydroxymethylene group and there is obtained a starting material of formula III where $R_2'$ is hydroxymethylene.

The etherification of a starting material of formula III can be carried out, when $R_2'$ represents a carboxyl group, by, for example, reaction with a lower alkanol in the presence of an acid (e.g., p-toluenesulfonic acid or boric acid) and, when $R_2'$ represents a carboxyl or hydroxymethylene group, by reaction with a lower alkyl halide. This etherification produces a compound of formula I where R is lower alkyl and $R_1$ is carboxyl.

When the etherification of the compound of formula III is carried out using an alcohol, the hydroxy moiety of the 1-hydroxyethyl group is etherified as is the hydroxy moiety of a hydroxymethylene group $R_2'$ which may be present in the starting material of formula III.

When the etherification is carried out using an alkyl halide, not only the hydroxy moiety of the 1-hydroxyethyl group but also the hydroxy moiety of a hydroxymethylene or carboxy group which may be present as $R_2'$ in the starting material of formula III is etherified.

When $R_2'$ in the compound of formula III represents a carboxyl group, the etherification can be carried out using an alkanol; for example, by dissolving the starting material of formula III in an alcohol furnishing the group R (e.g., methanol, ethanol or isopropanol) and heating the solution in the presence of an acidic agent at an elevated temperature, expediently at a temperature between about 60° C. and the boiling temperature of the mixture.

The etherification using an alkyl halide (e.g., methyl iodide or ethyl iodide) is conveniently carried out in the presence of a base (e.g., potassium carbonate) in an organic solvent (e.g., methyl ethyl ketone) at an elevated temperature, if necessary at the boiling point of the mixture.

The esterification of a starting material of formula III to produce a compound of formula I where $R_1$ is lower alkanoyl or aroyl can be carried out, for example, by treatment with a lower alkanoyl halide or aroyl halide (e.g., acetyl chloride) at a temperature between room temperature and the boiling point of the mixture. In so doing, a hydroxymethylene group which may be present as $R_2'$ in the starting material of formula III is esterified in addition to the 1-hydroxyethyl group.

An acid of formula I, i.e., where $R_1$ is carboxyl can be converted into the ester of formula I, i.e., where $R_1$ is alkoxycarbonyl or aralkoxycarbonyl, in a manner known per se, preferably by reaction with an appropriate aliphatic halide in the presence of a base such as potassium carbonate.

An acid of formula I, i.e., where $R_1$ is carboxy, can be reduced to a corresponding alcohol of formula I, i.e., where $R_1$ is hydroxymethylene in a manner known per se. The reduction can advantageously be carried out using a metal hydride or alkyl metal hydride in an inert solvent. Preferred hydrides are mixed metal hydrides such as lithium aluminum hydride and, especially, diisobutyl aluminum hydride or bis-(methoxy-ethyleneoxy)-sodium aluminum hydride. Suitable inert solvents are, inter alia, ether, tetrahydrofuran or dioxane when lithium aluminum hydride is used, and ether, hexane, benzene or toluene when diisobutyl aluminum hydride or bis-(methoxy-ethyleneoxy)-sodium aluminum hydride is used.

An ester of formula I obtained can be hydrolyzed in a manner known per se; for example, by treatment with an alkali, especially aqueous alcoholic sodium hydroxide or potassium hydroxide at a temperature between room temperature and the boiling point of the mixture.

An ester of formula I, i.e., where $R_1$ is alkoxycarbonyl or aroyloxycarbonyl can be reduced to a corresponding alcohol of formula I, i.e., where $R_1$ is hydroxymethylene under the same conditions mentioned hereinbefore for the reduction of an acid of formula I.

An alcohol of formula I, i.e., where $R_1$ is hydroxymethylene can be esterified to form the compound of formula I where $R_1$ is alkanoyloxymethylene or aroyloxymethylene by treatment with an alkanoyl halide or aroyl halide or with an anhydride, conveniently in the presence of a base (e.g., pyridine or triethylamine) at a temperature between room temperature and the boiling point of the mixture.

The polyene compounds of formula I are pharmacodynamically valuable compounds. They can be used for the topical and systemic therapy of tumors. They are, moreover, suitable for the topical and systemic therapy of acne, psoriasis and other dermatological affections occurring with an increased or pathologically altered cornification. The polyene compounds of formula I can also be used for combatting mucous membrane diseases with inflammatory or degenerative or metaplastic alterations.

The toxicity of the polyene compound of formula I is slight. The acute toxicities $LD_{10}$, $LD_{50}$ and $LD_{90}$ of 9-[2-(1-methoxyethyl)-5,5-dimethyl-cyclopent-1-en-1-yl]-3,7-dimethyl-nona-2,4,6,8-tetraen-1-acid are shown in the following Table which gives the delayed toxicity in mice after 20 days following the administration of 350 mg/kg i.p. in rape oil.

Table 1

|  | $LD_{10}$ mg/kg | $LD_{50}$ mg/kg | $LD_{90}$ mg/kg |
| --- | --- | --- | --- |
| after 1 day | >4000 | >4000 | >4000 |
| after 10 days | 290 | 350 | 430 |
| after 20 days | 290 | 350 | 430 |

The tumor inhibiting activity of the polyene compounds of formula I is significant. In the papilloma test, tumors induced with dimethylbenzanthracene and croton oil regress. The average sum of the diameter of the papillomae decreases within 2 weeks by 51% upon intraperitoneal administration of 25 mg/kg/week and by 80% upon intraperitoneal administration of 250 mg/kg/week.

The dosages contemplated for the use of the compound of the present invention vary according to the kind and route of application and according to the requirements of the patient. The compounds of formula I can be administered in amounts of from about 1 to 20 mg. daily in one or more doses. A preferred form of pharmaceutical preparation is capsules with a content of about 1 mg. to about 20 mg. of active substance. Capsules of hard or soft gelatin, methyl cellulose or of other suitable materials which dissolve in the digestive tract are suitable.

The pharmaceutical preparations containing the compound of formula I can also contain inert as well as medicinally active additives. Tablets or granules, for example, can contain suitable binding agents, fillers, carriers or diluents. Liquid agents can, for example, exist in the form of a sterile, water-miscible solution. Besides the active substance, capsules can additionally contain a filling material or thickening agent. Furthermore, there can also be present flavor-improving additives, preservatives, stabilizing agents, moisture-retaining agents or emulsifiers, salts for varying the osmotic pressure, buffers and other additives as recognized in the art of pharmaceutical compounding.

The pharmaceutically acceptable carriers and diluents mentioned hereinbefore can be organic or inorganic substances, for example, water, gelatin, lactose, starches, magnesium stearate, talc, gum arabic, polyalkylene glycols and the like.

For topical application, the compounds of formula I can expediently be used in the form of salves, ointments, tinctures, creams, solutions, lotions, sprays, suspensions and the like. Ointments and creams, as well as solutions, are preferred. These preparations serving for topical application can be manufactured by mixing the process products as the active ingredient with non-toxic, inert solid or liquid carriers suitable for the topical administration of medicinal agents by methods according to the art of pharmaceutical compounding. The preparations for topical application contain from about 0.01 to about 1% by weight, preferably from about 0.03 to about 0.3% by weight of the active substance. Salves or creams containing from 0.03 to 0.3% by weight of the compound of formula I are particularly preferred.

It is within the purview of the instant invention to incorporate into pharmaceutical preparations containing the active compounds enumerated herein an antioxidant such as, for example, tocopherols, N-methyl-$\gamma$-tocopheramine, as well as butylated hydroxyanisole, butylated hydroxytoluene or ethoxyquin.

The following examples are illustrative but not limitative of this invention. All temperatures are in degrees centigrade. The dilute sulfuric acid utilized in the Examples in about 2 N. The concentrated sulfuric acid is 96%.

EXAMPLE 1

5 g. of 9-[2-(1-hydroxyethyl)-5,5-dimethyl-1-cyclopent-1-en-1-yl]-3,7-dimethyl-nona-2,4,6,8-tetraen-1-acid are dissolved in 150 ml. of methanol. The solution is treated with 50 mg. of p-toluenesulfonic acid and concentrated to a volume of about 50 ml. The 9-[2-(1-methoxyethyl)-5,5-dimethyl-cyclopent-1-en-1-yl]-3,7-dimethyl-nona-2,4,6,8-tetraen-1-acid isolated from the concentrate melts at 197°–199° C. Absorption maximum: 363 nm; $E_{1cm}^{1\%} = 1650$ (ethanol).

EXAMPLE 2

By the procedure of Example 1, 9-[2-(1-hydroxyethyl)-5,5-dimethyl-1-cyclopent-1-en-1-yl]-3,7-dimethyl-nona-2,4,6,8-tetraen-1-acid is reacted with ethanol in the presence of p-toluenesulfonic acid or boric acid to produce 9-[2-(1-ethoxyethyl)-5,5-dimethyl-cyclopent-1-en-1-yl]-3,7-dimethyl-nona-2,4,6,8-tetraen-1-acid (melting point = 172°–174° C.). The compound 9-[2-(1-hydroxyethyl)-5,5-dimethyl-1-cyclopent-1-en-1-yl]-3,7-dimethyl-2,4,6,8-nona-tetraen-1-acid is reacted, by the procedure of Example 1, with isopropanol in the presence of p-toluene-sulfonic acid or boric acid to produce 9-[2-(1-isopropoxyethyl)-5,5-dimethyl-cyclopent-1-en-1-yl]-3,7-dimethyl-nona-2,4,6,8-tetraen-1-acid.

EXAMPLE 3

280 g. of vitamin A acid ethyl ester are dissolved in 2000 ml. of acetone and, while stirring at 0° to +5° C., treated with 1100 ml. of a solution of 267.2 g. of chromium trioxide and 230 ml. of concentrated sulfuric acid in 1000 ml. of water. The mixture is stirred for 0.5 hour at +5° C., then treated with 5000 ml. of water and exhaustively extracted with diethyl ether. The ether phase is washed neutral with a saturated aqueous sodium chloride solution, dried over sodium sulfate and evaporated under reduced pressure. The semi-crystalline residue is taken up in 750 ml. of methanol, stirred thoroughly and filtered. The 3,7,11,11-tetramethyl-10,15-dioxo-hexadeca-2,4,6,8-tetraen-1-acid ethyl ester remaining behind after evaportion of the filtrate is purified by adsorption on silica gel (elution agent: hexane/ethyl acetate — 4:1 parts by volume). Absorption maximum (rectified alcohol): 353 and 368 nm ($E_{1cm}^{1\%}$ = 1470 and 1355.

EXAMPLE 4

33.5 g. of 3,7,11,11-tetramethyl-10,15-dioxo-hexadeca-2,4,6,8-tetraen-1-acid ethyl ester are dissolved in 1000 ml. of ethanol and stirred for 16 hours at 50° C. with 13.5 ml. of 70% by weight of perchloric acid in water. The mixture is concentrated under reduced pressure, poured into a mixture of ice-water and sodium bicarbonate and exhaustively extracted with diethyl ether. The ether extract is washed neutral, dried and evaporated under reduced pressure. The residual dark yellow oil (31.5 g.) is purified by adsorption on a 60-fold amount of silica gel (elution agent: hexane/ethyl acetate — 3:1 parts by volume). The resulting 9-(2-acetyl-5,5-dimethyl-cyclopent-1-en-1-y1)-3,7-dimethyl-nona-2,4,6,8-tetraen-1-acid ethyl ester (yellow crystals) melts at 100° C. after recrystallization from hexane. Absorption maximum (ethanol): 386 nm ($E_{1cm}^{1\%}$ = 1680).

EXAMPLE 5

17g. of 9-(2-acetyl-5,5-dimethyl-cyclopent-1-en-1-yl)-3,7-dimethyl-nona-2,4,6,8-tetraen-1-acid ethyl ester are dissolved in 300 ml. of ethanol and stirred for 1 hour at 60° C. (bath temperature) with 17 g. of potassium hydroxide. The mixture is poured into ice-water and extracted with diethyl ether. The aqueous phase is made slightly acid with 3N aqueous sulfuric acid and exhaustively extracted with diethyl ether. This latter ether phase is washed neutral, dried and evaporated under reduced pressure. The residual 9-(2-acetyl-5,5-dimethyl-cyclopent-1-en-1-y1)-3,7-dimethyl-nona-2,4,6,8-tetraen-1-acid melts at 196°-198° C. after recrystallization from methanol or hexane/tetrahydrofuran. Absorption maximum (ethanol): 384 nm ($E_{1cm}^{1\%}$ = 1700).

EXAMPLE 6

2 g. of 9-(2-acetyl-5,5-dimethyl-cyclopent-1-en-1-yl)-3,7-dimethyl-nona-2,4,6,8-tetraen-1-acid are treated portionwise with a total of 3 g. of sodium borohydride after the addition of 70 ml. of 80% by volume methanol in 20% by volume water. The mixture is stirred for 90 minutes at room temperature and thereafter poured into ice-water. The aqueous mixture which reacts alkaline is shaken out with diethyl ether. The ether extract is discarded. The aqueous phase is acidified with dilute aqueous 3 N-sulfuric acid. The acidic solution is exhaustively extracted with ether. The ether extract is washed neutral with a saturated aqueous sodium chloride solution, dried over sodium sulfate and concentrated under reduced pressure. The 9-[2-(1-hydroxyethyl)-5,5-dimethyl-cyclopent-1-en-1-yl]-3,7-dimethyl-nona-2,4,6,8-tetraen-1-acid which separates from the concentrate in the form of yellow crystals melts at 152°-154° C. after recrystallization for ethanol.

EXAMPLE 7

6 g. of 9-[2-(1-methoxyethyl)-5,5-dimethyl-cyclopent-1-en-1-yl]-3,7-dimethyl-nona-2,4,6,8-tetraen-1-acid are dissolved in 100 ml. of methyl ethyl ketone. The solution is treated with 10 ml. of methyl iodide after the addition of 15 g. of potassium carbonate and heated to boiling under reflux conditions for 8 hours. The mixture is subsequently poured onto ice and exhaustively extracted with diethyl ether. The ether extract is washed with water, dried and evaporated under reduced pressure. The residual 9-[2-(1-methoxyethyl)-5,5-dimethyl-cyclopent-1-en-1-yl]-3,7-dimethyl-nona-2,4,6,8-tetran-1-acid methyl ester melts at 83°-85° C.

EXAMPLE 8

By the procedure of Example 7, from 9-[2-(1-ethoxyethyl)-5,5-dimethyl-cyclopent-1-en-1-y1]-3,7-dimethyl-nona-2,4,6,8-tetraen-1-acid there is produced 9-[2-(1-ethoxyethyl)-5,5-dimethyl-cyclopent-1-en-1-yl]-3,7-dimethyl-nona-2,4,6,8-tetraen-1-acid methyl ester. Absorption maximum: 363nm; $E_{1cm}^{1\%}$ = 1200 (ethanol).

EXAMPLE 9

5.9 g. of 9-[2-(1-ethoxyethyl)-5,5-dimethyl-cyclopent-1-en-1-yl]-3,7-dimethyl-nona-2,4,6,8-tetraen-1-acid methyl ester are dissolved in 100 ml. of absolute diethyl ether. The solution is treated at −50° C. with 500 mg. of lithium aluminum hydride in 18 ml. of absolute diethyl ether, after 30 minutes diluted with methanol, thereafter introduced into ice cold 2 N-sulfuric acid and extracted with diethyl ether. The ether extract is washed neutral, dried and evaporated under reduced pressure. The residual 9-[2-(1-ethoxyethyl)-5,5-dimethyl-cyclopent-1-en-1-yl]-3,7-dimethyl-nona-2,4,6,8-tetraen-1-ol is a light yellow oil. Absorption maximum: 326, 340, 358 nm; $E_{1cm}^{1\%}$ = 1415, 1800, 1430 (ethanol).

EXAMPLE 10

The 9-[2-(1-ethoxyethyl)-5,5-dimethyl-cyclopent-1-en-1-y1]-3,7-dimethyl-nona-2,4,6,8-tetraen-1-ol is reacted with p-phenylazobenzoyl chloride in the presence of pyridine. The resulting 9-[2-(1-ethyoxyethyl)-5,5-dimethyl-cyclopent-1-en-1-yl]-3,7-dimethyl-nona-2,4,6,8-tetraen-1-(p-phenylazobenzoate) melts at 121°-123° C.

EXAMPLE 11

3 g. of 9-[2-(1-ethoxyethyl)-5,5-dimethyl-cyclopent-1-en-1-yl]-3,7-dimethyl-nona-2,4,6,8-tetraen-1-ol are dissolved in 30 ml. of methylene chloride and, after the addition of 1.5 ml. of pyridine, treated at 0° C. with 1 g. of acetyl chloride in 5 ml. of methylene chloride. The mixture is stirred for 1 hour at room temperature, thereafter introduced into ice cold 2 N-sulfuric acid and diluted with methylene chloride. The methylene chloride phase is washed successively with water, with an aqueous 5% by weight sodium hydrogen carbonate solution and again with water, dried and evaporated under reduced pressure. The residual 9-[2(1-ethoxyethyl)-5,5-dimethyl-cyclopent-1-en-1-yl]-3,7-dimethyl-nona-2,4,6,8-tetraen-1-acetate is a yellow oil. Absorption maximum: 377, 341, 359, nm; $E_{1cm}^{1\%}$ = 1260, 1610, 1270 (ethanol).

EXAMPLE 12

7.3 g. of 9-[2-(1-hydroxyethyl)-5,5-dimethyl-cyclopent-1-en-1-yl]-3,7-dimethyl-nona-2,4,6,8-tetraen-1-ol are dissolved in 60 ml. of methylene chloride. After the addition of 7.5 ml. of pyridine, the solution is treated at 0° C. with a solution of acetyl chloride in 10 ml. of methylene chloride. The mixture is stirred for 16 hours at room temperature, thereafter poured onto ice and exhaustively extracted with diethyl ether. The ether extract is washed successively with N-sulfuric acid, with an aqueous 5% by weight sodium hydrogen carbonate solution and with water, dried and evaporated under reduced pressure. The residual 9-[2-(1-acetoxyethyl)-5,5-dimethyl-cyclopent-1-en-1-yl]-3,7-dimethyl-nona-2,4,6,8,-tetraen-1-acetate is a yellow oil. Absorption maximum: 325, 340, 358, nm; $E_{1cm}^{1\%}$ = 1250, 1610, 1840 (ethanol).

The following examples illustrate typical pharmaceutical preparations containing the polyene compounds provided by this invention.

EXAMPLE 13

A solution containing 0.1% active ingredient is prepared from the following components:

| | |
|---|---|
| 9-[2-(1-methoxyethyl)-5,5-dimethyl-cyclopent-1-en-1-yl]-3,7-dimethyl-nona-2,4,6,8-tetraen-1-acid | 0.1 g. |
| Ethanol (94%) | 70.0 g. |
| Propyleneglycol q.s. ad | 100.0 ml. |

EXAMPLE 14

A capsule composition containing the following ingredients is prepared:

| | |
|---|---|
| 9-[2-(1-methoxyethyl)-5,5-dimethyl-cyclopent-1-en-1-yl]-3,7-dimethyl-nona-2,4,6,8-tetraen-1-acid | 0.1 g. |
| Wax mixture | 51.4 g. |
| Vegetable oil | 103.0 g. |
| Trisodium salt of ethylenediamine tetraacetic acid | 0.5 g. |
| Individual weight of one capsule | 150 mg. |
| Active ingredient content of one capsule | 10 mg. |

EXAMPLE 15

A 0.3% salve containing the following ingredients is prepared:

| | |
|---|---|
| 9-[2-(1-methoxyethyl)-5,5-dimethyl-cyclopent-1-en-1-yl]-3,7-dimethyl-nona-2,4,6,8-tetraen-1-acid | 0.3 g. |
| Cetyl alcohol | 2.7 g. |
| Lanolin | 6.0 g. |
| White petroleum jelly | 15.0 g. |
| Distilled water q.s. ad | 100.0 g. |

EXAMPLE 16

A 0.3% water/fat emulsion containing the following ingredients is prepared:

| | |
|---|---|
| 9-[2-(1-methoxyethyl)-5,5-dimethyl-cyclopent-1-en-1-yl]3,7-dimethyl-nona-2,4,6,8-tetraen-1-acid | 0.3 g. |
| Magnesium stearate | 2.0 g. |
| Perhydrosqualene | 13.0 g. |

We claim:

1. A polyene compound of the formula:

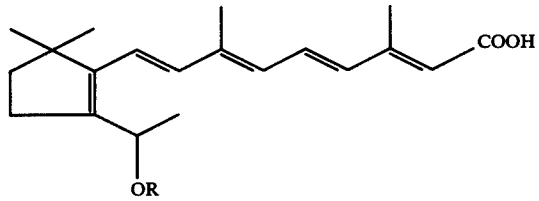

wherein R is lower alkyl.

2. The compound of claim 1 wherein said compound is 9-[2-(1-methoxyethyl)-5,5-dimethyl-cyclopent-1-en-1-yl]-3,7-dimethyl-nona-2,4,6,8-tetraen-1-acid.

3. The compound of claim 1 wherein said compound is 9-[2-(1-ethoxyethyl)-5,5-dimethyl-cyclopent-1-en-1-yl]-3,7-dimethyl-nona-2,4,6,8-tetraen-1-acid.

* * * * *